United States Patent
Mijers

(10) Patent No.: US 9,616,215 B2
(45) Date of Patent: Apr. 11, 2017

(54) ONE-WAY VALVE FOR AN INFUSION INSTRUMENT

(75) Inventor: Jan Willem Marinus Mijers, AL Haarlem (NL)

(73) Assignee: CEDIC S.R.L. (IT)

( * ) Notice: Subject to any disclaimer, the term of this patent is extended or adjusted under 35 U.S.C. 154(b) by 204 days.

(21) Appl. No.: 14/386,309

(22) PCT Filed: Mar. 20, 2012

(86) PCT No.: PCT/EP2012/054875
§ 371 (c)(1),
(2), (4) Date: Sep. 18, 2014

(87) PCT Pub. No.: WO2013/139374
PCT Pub. Date: Sep. 26, 2013

(65) Prior Publication Data
US 2015/0051554 A1    Feb. 19, 2015

(51) Int. Cl.
*A61M 39/24* (2006.01)
*A61M 5/142* (2006.01)

(52) U.S. Cl.
CPC ............. *A61M 39/24* (2013.01); *A61M 5/142* (2013.01)

(58) Field of Classification Search
CPC .. A61M 39/24; A61M 5/142; Y10T 137/7895
See application file for complete search history.

(56) References Cited

U.S. PATENT DOCUMENTS

| 4,593,720 A * | 6/1986 | Bergandy ............. B65B 39/001 137/859 |
| 6,036,171 A | 3/2000 | Weinheimer et al. |
| 2002/0117645 A1 | 8/2002 | Kiehne |

FOREIGN PATENT DOCUMENTS

| FR | 2910817 A1 | 7/2008 |
| WO | 03018105 A1 | 3/2003 |

* cited by examiner

*Primary Examiner* — Eric Keasel
(74) *Attorney, Agent, or Firm* — Jansson Munger McKinley & Kirby Ltd.

(57) ABSTRACT

The invention pertains to a one-way valve 1, especially for medical use, comprising at least one valve housing, an inlet 22, an outlet 26, and a valve element consisting of a valve body 20 and a valve seal 16. To it make possible for the one-way valve 1 to function reliably even in the case of liquids containing dietary fiber and for the tubing assembly to be filled rapidly, it is provided according to the invention that the valve body 20 comprises a passageway 21, which opens out into a sealing cavity 23 between the valve body 20 and the valve seal 16, and that the valve seal 16 comprises an opening 39, which can be closed in such a way by the valve body 20upon relative movement of two housing parts 2, 3 that the valve seal 16 rests with a sealing lip 28 against the valve body 20. As part of an infusion kit above the one-way valve 1, a feed pump is used, which produces a feed pressure for lifting the sealing lip 28 from the valve body 20, so that, after the passageway 21 has been closed, the feed pressure ensures a continuous flow of the infusion solution to the patient.

15 Claims, 9 Drawing Sheets

ONE-WAY VALVE FOR AN INFUSION INSTRUMENT

CROSS REFERENCE TO RELATED APPLICATIONS

This application is a national-phase entry under 35 USC §371 of International Application No. PCT/EP2012/054875, filed on Mar. 20, 2012. The entire disclosure and contents of this application are incorporated by reference into the present application.

The invention pertains to a one-way valve, especially for medical use, comprising at least one valve housing, an inlet, an outlet, and a valve arrangement consisting of a valve body and a valve seal.

One-way valves of the class in question for medical technology are needed for infusion sets, for example. This can be an infusion set which is first filled by gravity and which usually consists of a liquid container, which is elevated relative to the patient. The infusion solution is supplied to the patient through connecting tubing and an injection needle, wherein the flow of liquid can be adjusted by means of a tube clamp. Through the use of branches in the form of a T or a Y, for example, an infusion pump can be connected, which is used to supply a liquid medication, for example, to the patient at regular intervals. A similar situation exists in the case of the supply of enteral feeding solutions through a stomach tube. Here, too, the enteral feeding solution is supplied to the patient from a supply container through a tube leading to the stomach tube, wherein, in addition, an infusion pump can be used to supply liquid medications at regular intervals, or the enteral feeding solution can be conveyed by way of a pump, preferably a peristaltic pump. When a peristaltic pump is used, there is the possibility, in the simplest case, of placing the tube of the infusion set into an existing recess in the peristaltic pump, so that the peristaltic pump, with the help of a rotor, squeezes the tube and thus transports the liquid. The rotational direction of the peristaltic pump determines the direction in which the liquid is conveyed. Peristaltic pumps of this type are excellent ways of conveying enteral feeding solutions, for example, which can contain relatively large solid particles in some cases. For this reason, the peristaltic pump is usually arranged above the one-way valve so that the necessary feed pressure can be produced. With this arrangement, however, it must be ensured that no liquid can emerge from the possibly open end of the tube of the infusion set (anti-siphon solution) and that the feed pressure is sufficient to guarantee a continuous and interruption-free feed of the enteral feeding solution to the patient. In comparison to pure infusion solutions, enteral feeding solutions also comprise dietary fiber, which has a different consistency and can thus lead to a clogging of the one-way valve or to a blockage of the passageways present therein, as a result of which the one-way valve cannot fulfill its normal function.

To prevent the infusion solution and/or the medication from escaping from the infusion set under the force of gravity, one-way valves are used; on the one hand, such valves may not open until a certain necessary opening pressure is reached, whereas, on the other, they must prevent reflux back toward the infusion bag when the infusion set underneath the one-way valve is being flushed. Flushing is necessary after each enteral feeding to prevent the growth of bacteria in the infusion set. For this purpose, a T-branch or a Y-branch, to which a water-filled syringe can be connected, is installed underneath the one-way valve.

Beyond this, both in the case of infusion solutions and in the case of enteral feeding solutions, there is the problem that filling the entire infusion set is quite time-consuming, because filling the existing feed lines must proceed by gravity.

A valve for medical purposes is known from US Application No. 2007/0246674, which consists of two valve housing components and a piston. In the various embodiments, the piston can move axially within the two housing components when subjected to pressure, wherein the piston is sealed by sealing elements such as elements in the form of O-rings, for example. In addition, a seal is provided by a membrane located between the piston and the two housing components; the end surfaces of the membrane are held in a clamped state between the two housing components or between one housing component and the piston. The axial movement of the piston is used to cause the sealing element to change the size of the liquid space which is present.

It is therefore the object of the present invention to provide a one-way valve which avoids the problems known from the prior art.

According to the invention, the object is achieved in that the valve body comprises a passageway which opens into a sealable cavity between the valve body and the valve seal, and in that the valve seal comprises an opening which is closable in such a way by the valve body upon relative movement of two housing components that a sealing lip of the valve seal rests on the valve body in elastically liftable fashion. Additional advantageous configurations can be derived from the subclaims.

The solution according to the invention for forming a valve body with an additional passageway makes it possible to fill the entire tubing system of an infusion set much more quickly, so that, for example, a nurse will first connect the infusion solution or enteral feeding solution container by opening a tube clamp to fill the entire tube assembly and then exert manual pressure externally to close off the large existing passageway. This process is required only once when the infusion solution or the enteral feeding solution is connected. After the passageway has been closed, the one-way valve fulfills its normal function, so that the infusion solution or the enteral feeding solution is now conducted through an existing valve body with valve seal, wherein the pump used to implement this liquid transport can do so at the intended rate through cross sections which are much smaller. The essential advantage of this solution is that the filling and handling of the infusion set are simplified and accelerated, and thus a nurse, for example, requires much less time to complete the process. After the passageway has been closed, the only possibility, i.e., the only way liquid can be supplied to the patient, is for an infusion or peristaltic pump to build up a feed pressure sufficient to lift the sealing lip from the valve body; simultaneously it is ensured that, if a back pressure occurs on the valve outlet side and excess pressure therefore develops, the sealing lip will be pressed against the valve body, so that the infusion solution or flushing solution is prevented from being forced backward. This, i.e. the occurrence of excess pressure, is the case, for example, when the lower portion of the infusion set must be flushed in the direction toward the patient.

Another advantage of the one-way valve according to the invention is that, after the passageway has been closed, the infusion set is prevented from dripping, and only an adequate feed pressure will be able to open the valve seal.

It has been found to be especially advantageous here that, to maintain the normal function of the one-way valve, a valve body is used which is configured to support a sealing lip, wherein the valve seal is arranged a certain distance away from the valve body, as a result of which a cavity is formed. The cavity serves for filling with the infusion or enteral feeding solution, so that a relatively large open cross section is created which makes it easy to fill the tubing by gravity. As a preferred embodiment, a one-way valve is proposed which comprises both a passageway for the first-time filling and a cavity of large cross-sectional volume between the valve body and the valve seal, so that, even when an enteral feeding solution containing dietary fiber with its particulate matter is being supplied, the one-way valve will not become clogged, and a reliable closing of the sealing lip against the valve body is ensured. As a result of the special selection of a sealing lip and the avoidance of two-dimensional contact of the sealing element against the valve body, even relatively large particles such as roughage particles can therefore easily pass through the existing sealing section of the sealing lip versus the valve body under an appropriate feed pressure, and in particular the situation will not develop in which fiber particles become caught between the sealing lip and the valve body, which would interfere with the proper functioning of the one-way valve.

In elaboration of the invention, it is provided that the valve housing consists of at least two valve housing components, which are configured to be pushable or telescopable with respect to each other at least to some extent. The telescoping solution will always be used when the one-way valve is to be used first for rapid filling by gravity, wherein the passageway is open initially and is subsequently closed by the pushing-together of the two valve housing components. As a result of the relative movement between the two valve housing components, therefore, a suitably configured valve body will close off the passageway. The valve housing itself is configured as rotationally symmetric and aligned along a common axis, which is to say it has an elongated shape, wherein lengths of tubing can be connected to each end. It is also conceivable that part of the valve housing could be rotationally symmetric and another part configured as an angled section, such as a section extending at a right angle, so that the upper feed tube will be directly connected to the rotationally symmetric valve housing component, whereas the other length of tubing can be connected to the second valve housing component, i.e., the component configured at an angle.

In elaboration of the invention, it is provided that a first valve housing component is connected integrally to a centrally arranged valve body. The valve body is located inside a first valve housing component, wherein, in a special elaboration, the valve body is connected to the valve housing component by radial webs or bars, so that openings of sufficiently large dimensions are formed between the radial webs, through which openings the liquid can pass.

In further elaboration, the valve body has an inlet, which leads or opens to the passageway, and an outlet underneath the valve opening. The valve body and the valve seal are located between the inlet and the outlet, the valve seal resting against the valve body after the two valve housing components have been pushed together. The valve body consists here of a plastic part, preferably of a plastic part integrally connected to the valve housing component. The valve seal consists of an elastic material, which rests against the valve body and which, because of its elasticity, can be lifted when subjected to positive pressure. For closing the passageway, the valve body is pressed into the valve seal when the two valve housing components are pressed together, so that the sealing lip of the valve seal comes to rest on a conical contact surface of the valve body. The valve body can be connected to the valve housing component by radial webs or bars. In the case of an angled configuration, however, there is the possibility that the valve body could project from a radial surface. In both cases, it is ensured that, after the passageway inside the two valve housing components has been closed, the liquids passing through the sealing lips will arrive at the outlet. The sealing lip in this case contacts the valve body along a contact line, with the capacity to be lifted elastically, so that even relatively large particles of dietary fiber can pass through the valve seal under the action of a feed pressure.

So that the two valve housing components can be pushed together to close the passageway, one valve housing component comprises a pressure area for a thumb, for example, whereas the second valve housing component comprises a counter support area. The counter support area can consist of a flange collar or a radial surface, which is provided so that the index and middle fingers can rest on it; the thumb can be used to press the two components of the one-way-valve together and thus to close the passageway after the filling operation, whereupon only the function of the one-way-valve remains in effect.

For preassembly and for holding the two housing components together after the appropriate pressure has been applied, one housing component, in further elaboration of the invention, has one or more latching notches on an outside surface, whereas the corresponding valve housing component comprises one or more circumferentially distributed latching projections. The latching projections serve here to hold the two valve housing components together and can slide from a first latching notch, which is defined for preassembly, into another latching notch, wherein preferably sharp-edged latching projections are used, so that secure retention in each of the individual latching notches is guaranteed. The latching projections and latching notches are also intended for only a single use, because it is not intended that the pushed-together one-way-valve will ever be opened again later. Such one-way-valves are preferably provided for one-time use on a patient and must then be disposed of for hygienic reasons.

To prevent the two valve housing components from being pushed together unintentionally, it is possible to provide, in elaboration of the invention, a safety element, which is inserted into an existing recess in the area of the latching notches which serves to lock the two valve housing components together. The safety element consists, for example, of a segment of a circular ring with a gripping piece and can thus be placed onto a valve housing from the outside, namely, in the area of the latching notches, to block them. After removal of the safety element, which is also intended for only a single use, the two valve housing components can be pushed together.

In further elaboration of the invention it is provided that between the valve housing components a valve seal is arranged which lies in an undercut or socket made in the first valve housing component, and is held in position by a stop surface, and rests sealingly with at least one first sealing ridge on the second valve housing component and with a sealing lip on the valve body. The valve seal provided for the invention is simultaneously used to seal the two valve housing components against each other and also to create a seal against the valve body. For this reason, the valve seal lies in the undercut or socket in the first valve housing component, and at least one first sealing ridge rests sealingly against the second valve housing component. In general, the valve housing component are either clipped together or welded together after assembly, or, in the case of the solution described above, held together by latching projections and latching notches if a radial displacement of the two valve housing components is desired at a later point. To increase the effectiveness of the sealing action, this first seal can comprise several sealing ridges which can rest under pressure against an axial surface of a valve housing component, whereas the sealing lip rests against the valve body and is configured elastically so that it can be lifted from the valve body to allow the infusion liquid or enteral feeding liquid to pass through the valve opening formed between the valve body and the sealing lip. In the same way that the valve housing components are configured as rotationally symmetric parts, so, too, does the valve body have a rotationally symmetric form and is connected integrally to a valve housing component, wherein at least one entrance opening leads from the inlet of a first valve housing component to the cavity. It is conceivable here that, because of the way in which the valve body is attached inside the valve housing, several entrance openings are formed, all of which open out into the cavity.

Once the two valve housing components have been pushed together, the flow of the supplied enteral feeding or infusion solution is interrupted. Starting from the inlet, the flow direction leads to the entrance openings of the valve body and continues to the sealing lip resting on the valve body, wherein, as a result of a buildup of pressure by an infusion or peristaltic pump, the lifting of the sealing lip from the valve body establishes a connection with the outlet. Thus, the infusion pump, which acts on the enteral feeding or infusion solution, is able to open the valve. When a backpressure builds up, such as during a flushing operation below the one-way valve, the flow is blocked, because the increasing positive pressure presses the valve seal against the valve body. According to the principle of the structure of the infusion set, the infusion or peristaltic pump is installed above the one-way valve, so that, proceeding from the infusion bag, a conveying pressure is built up, which acts on the one-way valve and opens the sealing lip resting against the valve body. Depending on the type of infusion pump, there exists for this purpose, for example, the possibility of connecting the pump by way of a T-shaped or Y-shaped branch; or, if a peristaltic pump is used, part of the tube is laid in a guide of the peristaltic pump, and the transport of the enteral feeding or infusion solution in one direction is initiated by an actuating rotor, which acts directly on the tube. The conveying pressure developing here is sufficient to lift the valve seal from the valve body, wherein simultaneously, as a result of the pressure difference attributable to present between the area above and the area below the nonreturn function of the one-way valve is fulfilled.

The valve seal used is also rotationally symmetric and coaxially surrounds the valve body, wherein an inward-facing sealing lip rests elastically directly on the valve body, so that the closing and opening function of the valve is ensured. The pretension, that is, the pressure required to lift this sealing lip, can be determined on the basis of the diameter of the valve body, the thickness of the sealing lip, or the inside diameter of the sealing lip, so that the desired pretension can be adjusted. Alternatively, the elasticity and thus the opening pressure can additionally be determined by way of the Shore hardness of the selected sealing material, wherein the sealing lip is lifted from the valve body when the pressure builds up to about 20 to about 300 kPa, so that the infusion or enteral feeding solution can flow downward through the one-way valve under the feed pressure. Sealing materials with a Shore hardness of 60-80 SH-A are preferably used for the valve seal, so that a certain minimum pressure is required to lift the sealing lip from the valve body. As a result, it is ensured that any after-flow or dripping of the infusion solution under the effect of gravity is avoided.

The invention is explained again below on the basis of the figures.

Figure 1:
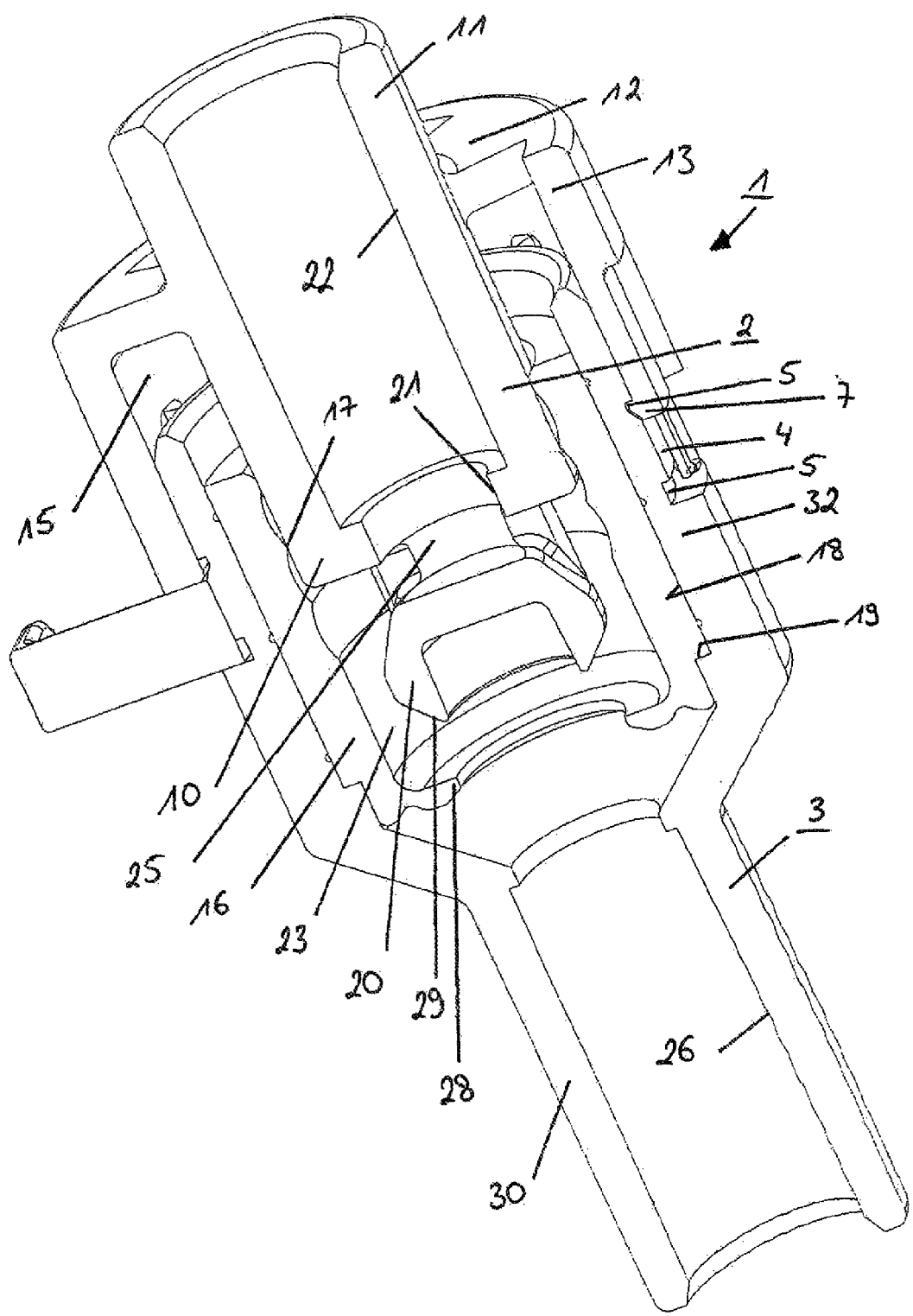
FIG. 1 shows a perspective cross-sectional side view of a one-way valve according to the invention.

FIG. 1 shows a perspective cross-sectional side view of a one-way valve 1, which, in the exemplary embodiment shown here, consists of a valve housing component 2 and a valve housing component 3. The two valve housing components 2, 3 are configured so that they telescope into each other, wherein the valve housing component 3 comprises, on an external surface 4, latching notches 5, into which the latching projections 7 of the other valve housing component 2 engage. The two valve housing components 2, 3, are to this extent telescoping, as is possible in the axial direction as a result of the latching projections 7 and latching notches 5 shown.

The first valve housing component 2 consists of a middle housing part 10, which merges at the outer end with a conically tapered socket or connector 11, onto which, for example, a tube can be slid or pushed. The housing part 10 is connected to the outer housing ring 13 by radial connecting struts 12, wherein the connecting struts 12 are formed around the entire circumference of the valve housing component 2. The upper valve housing component 2 has an end surface 14, which can be used to push the two valve housing components 2, 3 together. The index and middle fingers, for example, can, for this purpose, be placed on the end surface 14. The valve housing component 2 also comprises a recess 15, which is formed by the housing part 10 and the housing ring 13 and is provided to accommodate a valve seal 16 and the second valve housing component 3. The valve seal 16 sealingly contacts with its several sealing ridges 17 an interior circumferential surface of the housing part 10. The valve seal 16 is formed rotationally symmetric and consists of a hollow body, which is seated, furthermore, in an undercut 18 in the valve housing component 3 and rests for support against a contact shoulder 19. A rotationally symmetric valve body 20 is connected integrally to the first valve housing component 2 underneath the housing part 10. The valve body 20 is connected to the valve housing component 2 by several circumferentially distributed webs or bars 25 in such a way that, between the webs 25, openings 27 are formed, which establish a connection to a cavity 23 between the valve body 20 and the valve seal 16. This cavity 23 is initially open to the outlet 26 and is closed by contact of a sealing lip 28 against a conical contact surface 29 of the valve body 20, which occurs when the two valve housing components 2, 3 are pushed together; because of the elasticity of the valve seal 16 and of the sealing lip 28, it is therefore possible for the lip to be lifted for the purpose of allowing the passage of liquid, which leads to a sealing valve function when the pressure increases on the outlet 26 side. In the exemplary embodiment shown here, the valve housing component 2 has a passageway 21, which opens out at one end into the inlet 22 and at the other end into the cavity 23 through the openings 27 and then into the outlet 26. Between the valve body 20 and the valve seal 16, a cavity 23 is formed, which is bounded on one side by the shape of the valve body 20 and on the other side by the shape of the valve seal 16, wherein this cavity can be closed at the bottom by the sealing lip 28. At the top of the space, openings 27 are formed in a ring underneath the middle housing part 10 of the first valve housing component 2, so that the incoming liquid passes through the inlet 22 and the openings 27 before arriving in the cavity 23; and, after the two valve housing components 2, 3 have been pushed together and the cavity 23 has thus been closed, the sealing lip 28 can be lifted from the valve body 20 as a result of a pressure buildup produced by, for example, an infusion pump, and the liquid can thus escape to the area underneath the valve body 20.

The second valve housing component 3 also has a rotationally symmetric configuration and consists essentially of a hollow body with a connector 30, which comprises the outlet 26. The connector 30 is also provided so that a tube can be pushed or slid onto it, which means that the one-way valve 1 can thus be inserted into a length of tubing. Above the connector 30, the valve housing component 3 has a radially expanded housing ring 32, which carries the latching notches 5 on its external surface 4 and receives the first valve housing component 2.

The one-way valve 1 according to the invention is delivered in the form shown in FIG. 1, namely, with an unclosed cavity 23, which leads at one end to the inlet 22 via the cut-outs 27 and at the other end to the outlet 26. As a result of this configuration, it is ensured, for example, that the infusion solution or an enteral feeding solution can pass directly from a supply container (not shown) into the one-way valve 1 and from there into an additional length of tubing via the inlet 22 of the one-way valve 1 and via the open cavity 23, so that the overall infusion set can be filled in accelerated fashion. After all of the lengths of tubing have been filled, the cavity 23 can be closed by manually pushing together the two valve housing components 2, 3, so that the infusion or enteral feeding solution can now flow only laterally, via the valve body 20, into the cavity 23 and from there can reach the outlet only after the increasing pressure caused by the action of the infusion or peristaltic pump on the liquid brings about an opening of the sealing lip 28 versus the valve body 20. In addition, a T-branch or a Y-branch can be provided upstream (relative to the flow direction) of the one-way valve, so that, for example, an infusion pump can be connected to meter a medication for a limited period of time, or so that a peristaltic pump can be used to convey an enteral feeding solution. Thus the liquid passes via the cavity 23 into the outlet 26, wherein the flow rate can be adjusted by means of additional devices (not shown) such as tube clamps.

Thanks to the use of the one-way valve 1, the sealing lip 28 of the valve seal 16 is pressed against the valve body 20 when there is a back pressure resulting from a higher pressure in the lower area of the tubing system, wherein it is possible for this pressure to be higher than that produced by the infusion pump. Backflow into the supply container is thus prevented. Only when the feed pressure is higher than that in the lower area of the tubing system can the valve element 16 open and the infusion or enteral feeding solution start to flow again through the one-way valve 1 to the patient.

The one-way valve 1 according to the invention thus makes it possible, first, to fill the tubing assembly quickly when, for example, a stomach tube or an injection needle is to be used; in addition, after manual closure, that is, after the two valve housing components 2, 3 have been pushed together, the one-way valve can be used as a normal one-way valve, so that, as a result of excess pressure developing underneath the one-way valve 1, backflow into the infusion or enteral feeding container can be excluded. The effect of the infusion or peristaltic pump consists essentially in building up an appropriate feed pressure, namely, a pressure acting from the infusion bag to the one-way valve, so that the sealing lip can be lifted from the sealing body by the feed pressure and the infusion or enteral feeding liquid can arrive in the patient via the one-way valve. If a backup or back pressure occurs underneath the one-way valve, the function of the one-way valve prevents the infusion solution from being forced in the direction of the infusion bag.

Figure 2:
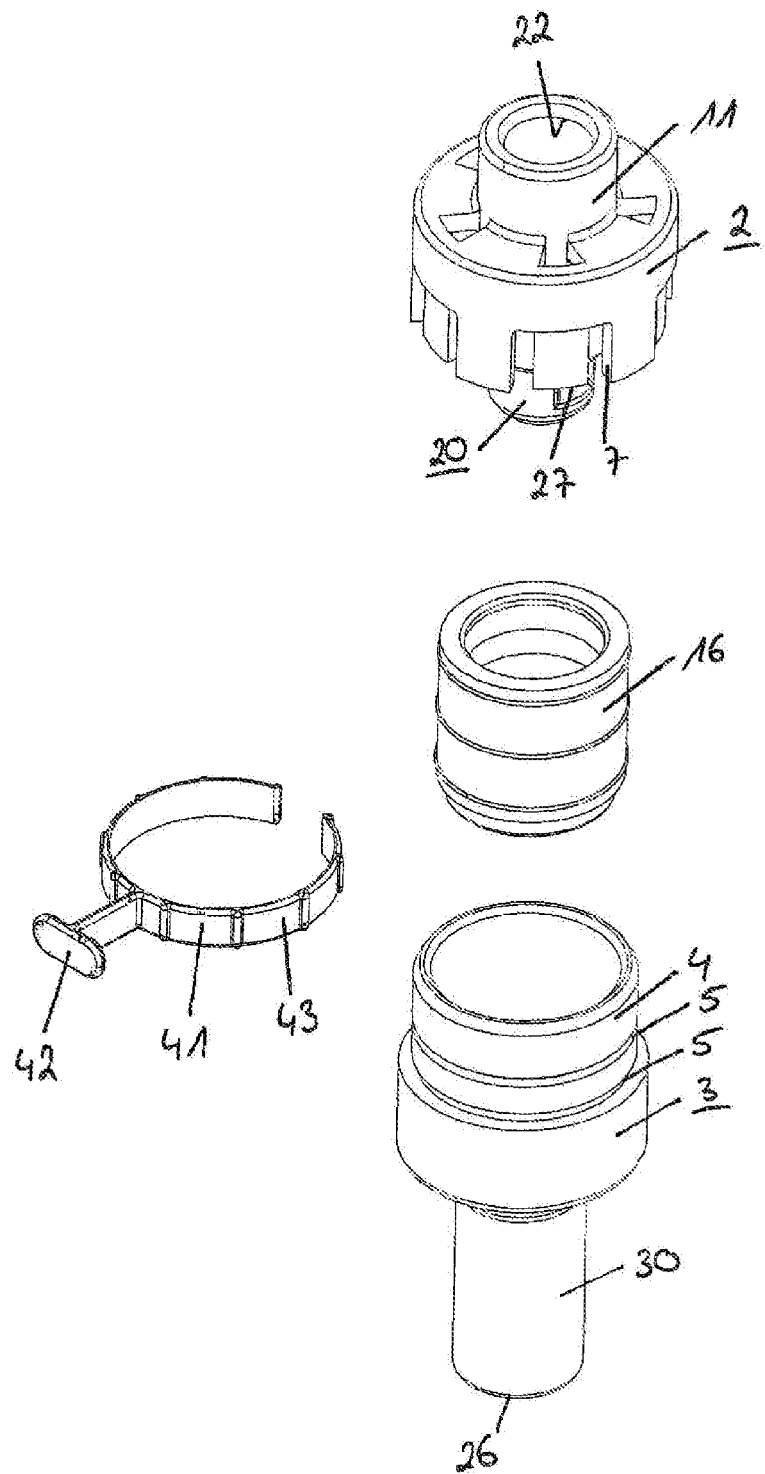
FIG. 2 shows an exploded view of the one-way valve according to FIG. 1 with all the individual parts.

FIG. 2 shows an exploded, perspective view of the one-way valve 1 according to the invention, consisting of a first valve housing component 2 with socket 11 and a second valve housing component 3 with connector 30. The socket 11 forms the inlet 22, whereas the connector 30 comprises the outlet 26. The valve seal 16 is also rotationally symmetric, and for assembly is first pressed into the undercut 18 in the second valve housing component 3; then the first valve housing component 2 is pressed into the valve seal 16, the sealing lips 17 thus making contact with it, until the latching projections 7 engage in the latching notches 5 present in the second valve housing component 3. It is provided here that the projections engage first in the first latching notch 5, so that a large flow-through opening according to the description of FIG. 1 is present. Before the two valve housing components 2, 3 are brought together, a safety element 41 with a gripping piece 42 and an incompletely closed circular ring 43 is placed onto the second valve housing component 3, so that, for example, the lower latching notch 5 is covered. Thus the valve housing component 2 can be pushed toward the valve seal 16 only as far as the first latching notch 5. Simultaneously, it is ensured by this measure that a large-volume passageway is present between the inlet 22 and the outlet 26 for the first-time filling of the tubing assembly. After the tubing has been filled, the safety element 41 can be pulled off and thus removed, and when the two valve housing components 2, 3 are now pushed together all the way, the sealing lip 28 makes contact with the valve body 20, as described with respect to FIG. 1, which both ensures the valve function of the one-way valve 1 and makes it possible for liquid to be conveyed from the inlet 22 to the outlet 26 when the pressure builds up enough to lift the sealing lip 28 from the valve body 20.

Figure 3:
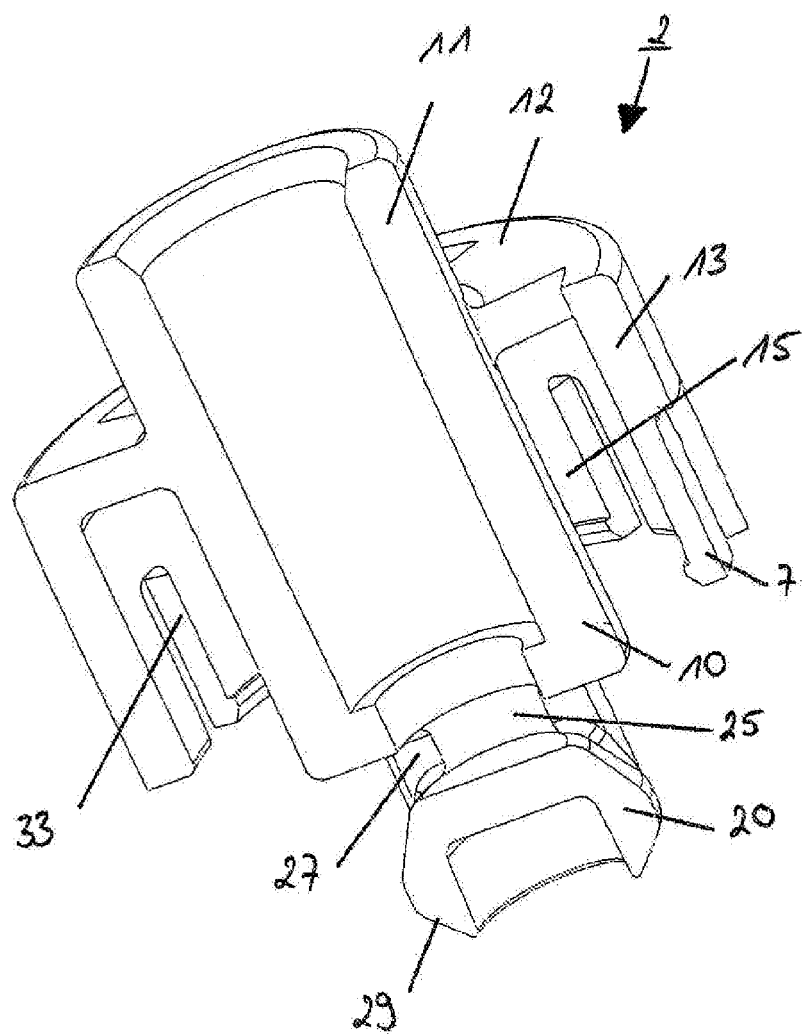
FIG. 3 shows a perspective cross-sectional side view of a first valve housing component.

FIG. 3 shows a perspective cross-sectional side view of the first valve housing component 2 with its interior housing part 10 and the external housing ring 13 as well as the valve body 20. The valve body 20 is connected integrally to the valve housing component 2, namely, by way of webs or bars 25, which are distributed around the circumference so that openings 27 remain between the individual webs 25. The valve body 20 is formed rotationally symmetric and comprises, on the bottom, a conical contact surface 29. The contact surface 29 serves to make contact with the sealing lip 28 of the valve seal 16. At the top of the valve housing component 2, the housing part 10 terminates in the socket 11, onto which a tubing assembly can be pushed. The housing part 10 and the housing ring 13 are connected integrally to each other by webs 12, wherein the webs 12 are also distributed around the circumference. Between the housing part 10 and the housing ring 13, a recess 15 is formed, which is provided to receive the second valve housing component 3 and the valve seal 16. The circular ring 13 also comprises circumferentially distributed latching projections 7, which are formed by slot-like recesses 33 in the housing ring 13. Thus the elasticity of the individual latching projections 7 is sufficiently guaranteed.

Figure 4:
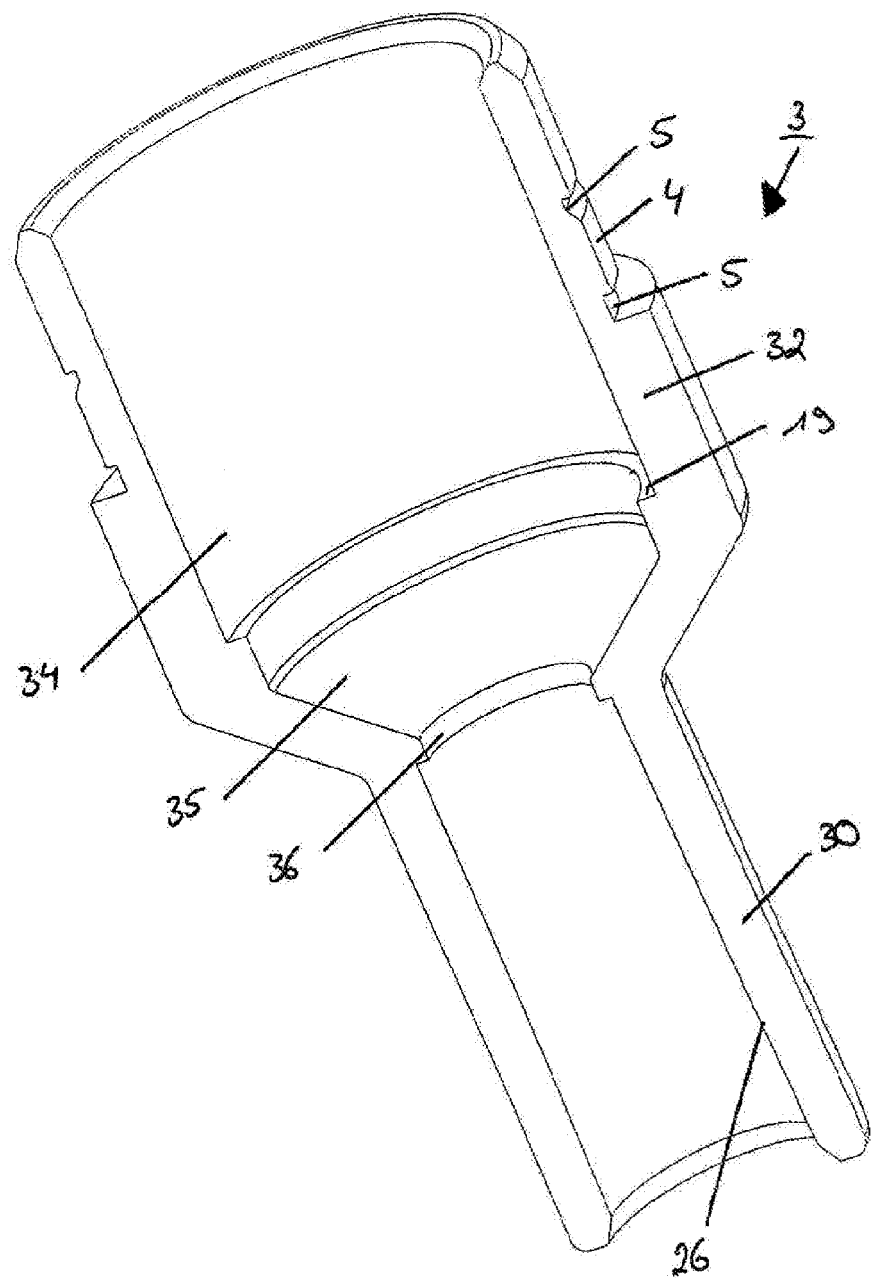
FIG. 4 shows a perspective cross-sectional side view of a second valve housing component.

FIG. 4 shows a perspective cross-sectional view of the second valve housing component 3, which is configured as a hollow cylinder consisting of a connector 30 with the outlet 26 and a housing ring 32. On the external surface 4 of the housing ring 32, two latching notches 5 are formed, which are provided to receive the latching projections 7 of the first valve housing component 2. A contact shoulder 19 serves to give the inserted valve seal 16 axial support, whereas the valve seal 16 also comes to rest against the inner ring surface 34. The transition from the housing ring 32 to the connector 30 is accomplished here by a conical surface 35, which leads via an opening 36 directly to the outlet 26.

Figure 5:
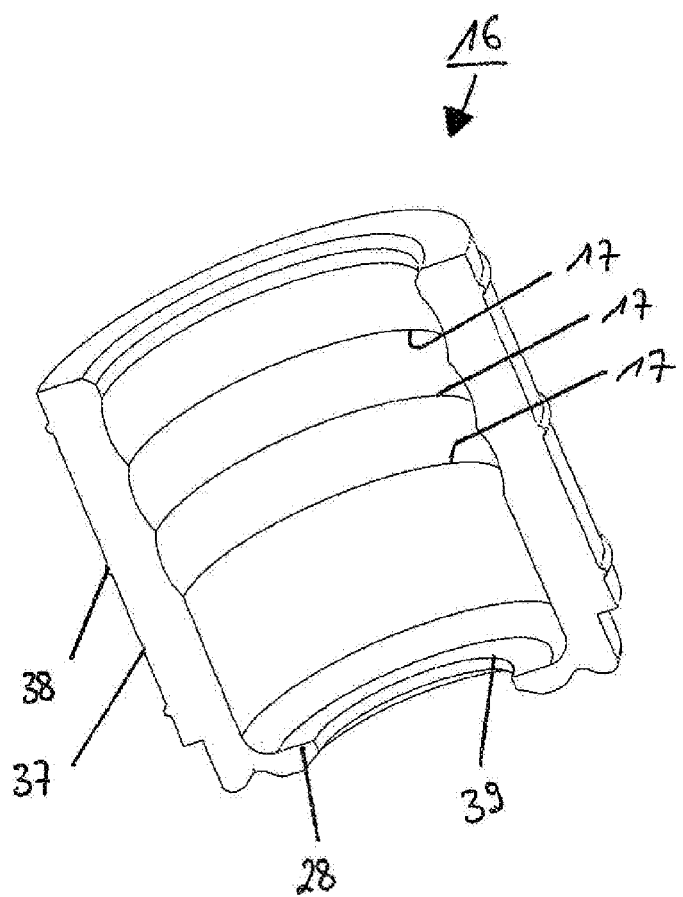
FIG. 5 shows a perspective cross-sectional side view of the valve seal.

FIG. 5 shows a perspective cross-sectional view of the valve seal 16, which consists of an elastic material and is also configured in the shape of a ring. On the inside surface, several sealing ridges 17 are formed, which are provided for direct contact against the housing part 10 of the first valve housing component 2.

On the external surface 37 are several sealing rings 38, which are provided for contact against the housing ring 32 of the second valve housing component 3. The valve seal 16 also comprises a circular ring-shaped opening 39, which is bounded by a sealing lip 28. The sealing lip 28 serves to make contact with the valve body 20 of the first valve housing component 2.

Figure 6:
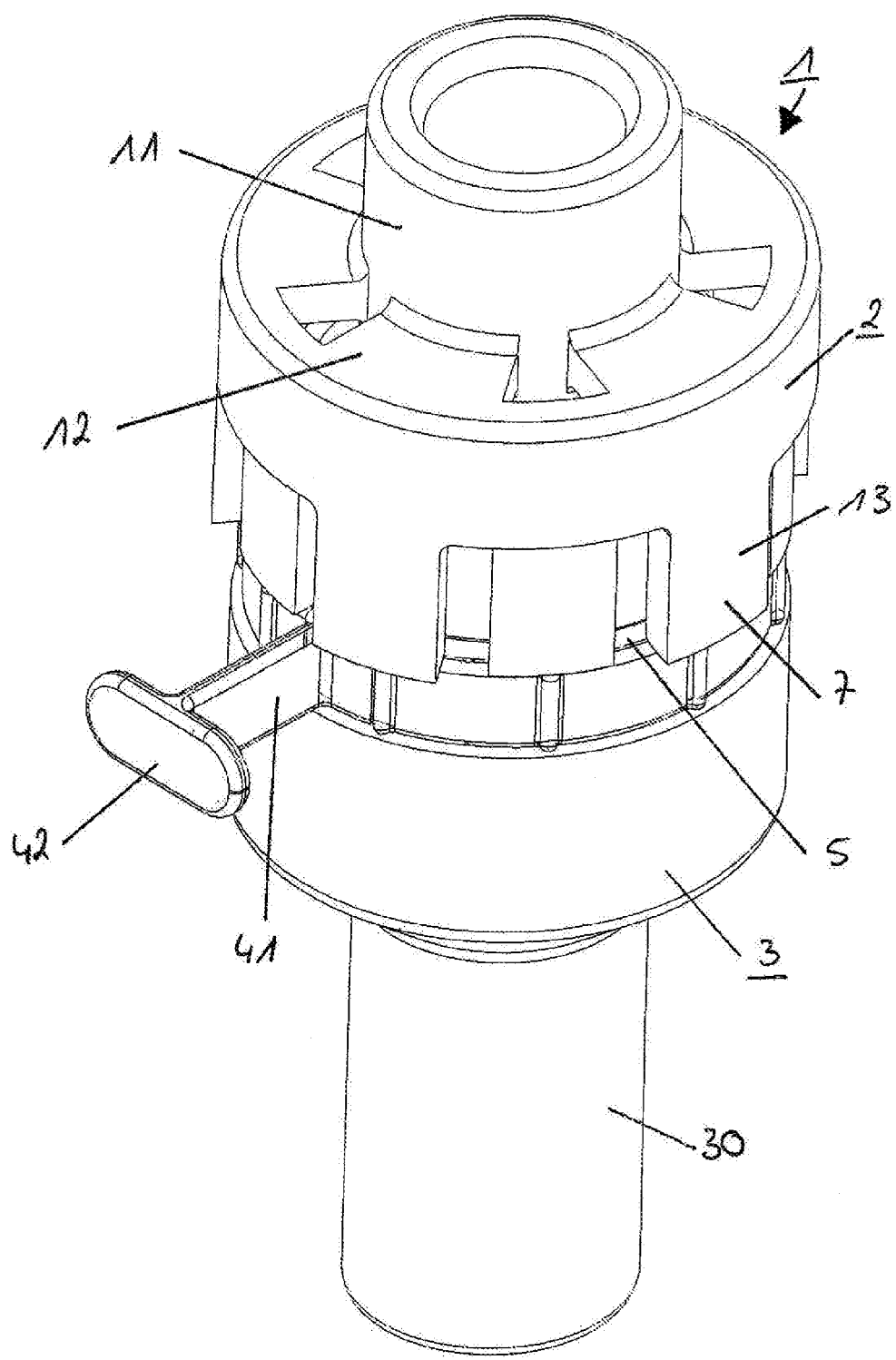
FIG. 6 shows a perspective side view of the one-way valve from FIG. 1 with a safety element.

FIG. 6 shows a perspective side view of the one-way valve 1 according to the invention after assembly, consisting of the first valve housing component 2 and the second valve housing component 3. Between the two valve housing components 2, 3, the safety element 41 with gripping piece 42 is arranged, so that, after the safety element 41 has been pulled off, it is possible to push the two valve housing components 2, 3 together all the way. The one-way valve 1 can be connected here to the tubing assembly by way of the upper socket or connector 11 and the lower connector 30. It is also possible to see again in this view that the connector 11 is connected to the housing ring 13 by circumferentially distributed webs 12. It can also be clearly seen how the latching projections or retaining claws 7 engage in the ring-shaped latching notch 5 of the other valve housing component 3.

Figure 7:
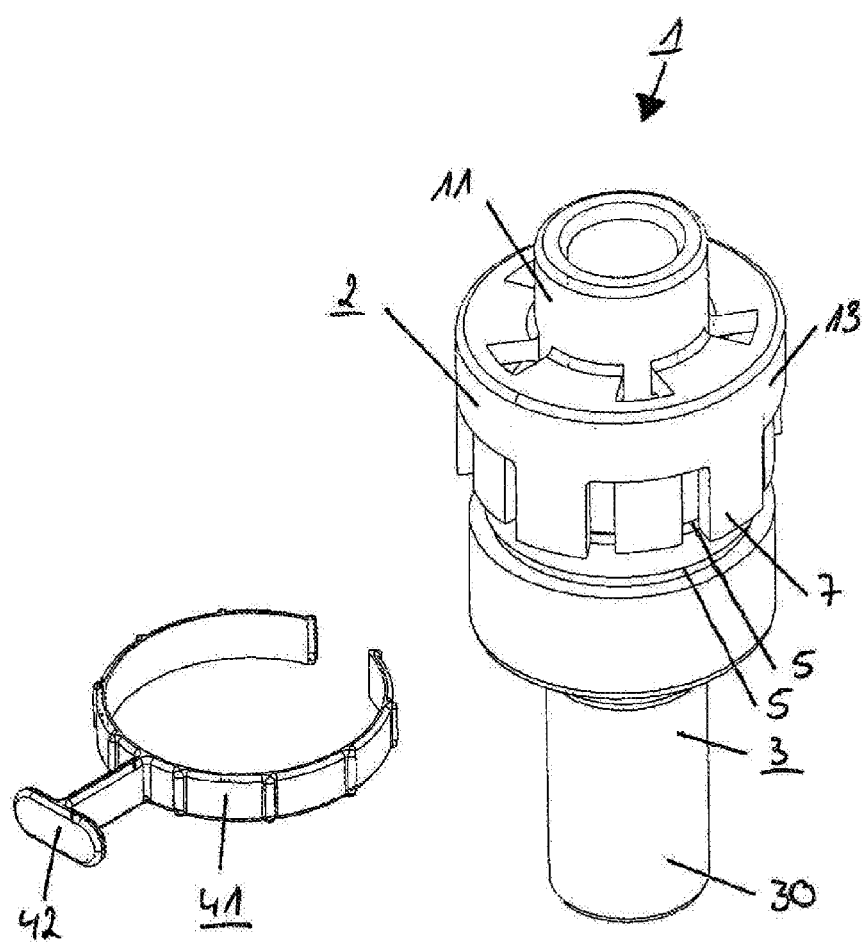
FIG. 7 shows a perspective side view of the one-way valve according to FIG. 6 after removal of the safety element.

FIG. 7 shows the one-way valve 1 according to FIG. 6 after the safety element 41 has been removed. In this diagram, the two valve housing components 2, 3 have not yet been telescoped into each other, because the latching projections 7 are still located in the upper latching notch 5.

Figure 8:
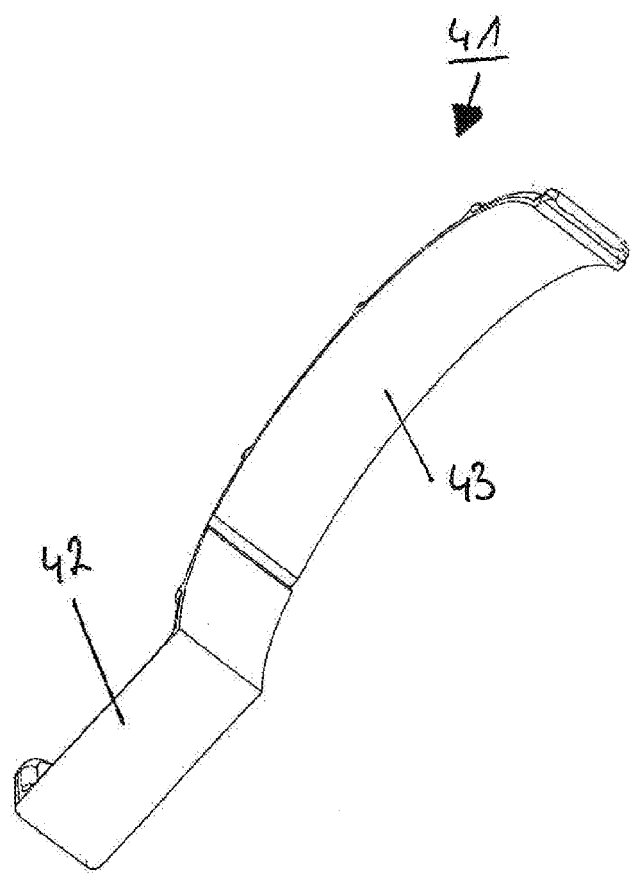
FIG. 8 shows a perspective cross-sectional side view of the safety element.

FIG. 8 shows another perspective cross-sectional view of the safety element 41, consisting of a gripping piece 42 and an incompletely closed circular ring section 43. The width of the safety element 41 is adapted here to the distance between the two latching notches 5 of the first valve housing component 2 Like the other parts of the one-way valve 1, the safety element 41 consists of an elastic plastic part, so that the safety element 41 can be pulled off easily from the one-way valve 1.

Figure 9:
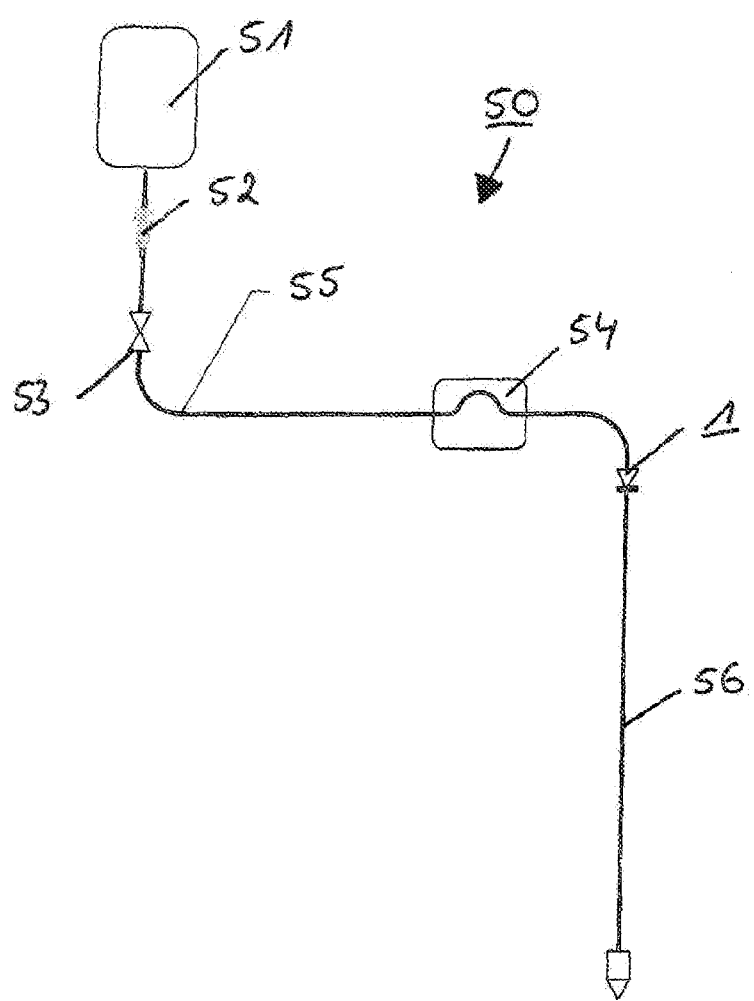
FIG. 9 shows a schematic diagram of the structure of an infusion set with infusion pump.

FIG. 9 shows a schematic diagram of an infusion set 50, which consists of an infusion bag 51 with a connecting line 52 and a tube clamp 53 on one side and a peristaltic pump 54 and a one-way valve 1 according to the invention on the other side. A tube connection 55 leads first from the infusion bag 51, via the connecting line 52 and the tube clamp 53, to the peristaltic pump 54. The peristaltic pump 54 can, in the simplest case, use a rotor to exert a force on the elastic tube connection 55 to develop a feed pressure acting on the infusion solution. This feed pressure is itself sufficient to lift the sealing lip of the one-way valve 1 from the sealing body, so that the infusion solution can be supplied to the patient via a tube 56.

The invention claimed is:

1. A one-way medical valve device including at least one valve housing, an inlet, an outlet, and a valve arrangement having a valve body and a valve seal wherein the improvement comprises:
   the housing being formed by first and second relatively-movable housing components;
   the valve body having a passageway which opens into a sealable cavity between the valve body and the valve seal; and
   the valve seal which is a hollow body including (a) a tubular portion between the first and second housing components and configured to seal the first and second housing components against each other and (b) an elastically-liftable sealing lip integral with and extending from the tubular portion and defining an opening which is closable by the valve body upon relative movement of the two housing components, the sealing lip engaging the valve body in elastically-liftable fashion.

2. The one-way valve device of claim 1 wherein the first and second housing components are configured to be at least relatively movable by partially telescoping motion with respect to each other.

3. The one-way valve device of claim 2 wherein one of the housing components has a pressure area and the other has a counter support area, the pressure area and the counter support area being for manually causing relative movement of the housing components with respect to one another.

4. The one-way valve device of claim 1 wherein the valve seal rests in an undercut in the second housing component against a contact shoulder thereof, and rests sealingly against the first housing component, the valve seal having with at least one sealing ridge against the first housing component.

5. The one-way valve device of claim 1 wherein the valve seal is rotationally symmetric and the elastically-liftable sealing lip extends radially inwardly for its engagement with the valve body.

6. The one-way valve device of claim 1 wherein the valve body is rotationally symmetric and is integral with the first housing component.

7. The one-way valve device of claim 1 wherein the valve body includes a conical contact surface for the valve seal.

8. The one-way valve device of claim 1 wherein the sealing lip engages the valve body along a contact line.

9. The one-way valve device of claim 1 wherein the inlet opens out into the sealable cavity and the outlet is located underneath the valve seal.

10. The one-way valve device of claim 1 wherein the flow direction starting from the inlet leads via an opening of the valve body to the sealing lip, whereby, as a result of the buildup of pressure, lifting of the sealing lip from the valve body establishes a connection to the outlet.

11. The one-way valve device of claim 1 wherein the valve seal has a Shore hardness of 60-80 SH-A.

12. A one-way medical valve device including at least one valve housing, an inlet, an outlet, and a valve arrangement having a valve body and a valve seal wherein the improvement comprises:

the housing being formed by first and second relatively-movable housing components, one of the housing components including one or more latching notches on an external surface thereof and the other having one or more circumferentially distributed latching projections engageable with the latching notches;

the valve body having a passageway which opens into a sealable cavity between the valve body and the valve seal; and the valve seal having an elastically-liftable sealing lip defining an opening which is closable by the valve body upon relative movement of the two housing components, the sealing lip engaging the valve body in elastically-liftable fashion.

13. The one-way valve device of claim 12 wherein the latching projections are lockable by a removable safety element.

14. The one-way valve device of claim 13 wherein the safety element comprises a circular ring segment with a gripping piece.

15. A one-way medical valve device including at least one valve housing, an inlet, an outlet, and a valve arrangement having a valve body and a valve seal wherein the improvement comprises:

the housing being formed by first and second relatively-movable housing components;

the valve body having a passageway which opens into a sealable cavity between the valve body and the valve seal; and the valve seal having an elastically-liftable sealing lip defining an opening which is closable by the valve body upon relative movement of the two housing components, the sealing lip engaging the valve body in elastically-liftable fashion, the valve seal (a) being arranged between the first and second housing components, (b) resting in an undercut in the second housing component against a contact shoulder thereof, (c) resting sealingly against the first housing component, the valve seal including several inward-facing sealing ridges pressably against an axial surface of the first housing component.

* * * * *